US009878013B2

(12) United States Patent
Debinski et al.

(10) Patent No.: US 9,878,013 B2
(45) Date of Patent: Jan. 30, 2018

(54) IL-13 RECEPTOR BINDING PEPTIDES

(71) Applicant: Wake Forest University Health Sciences, Winston-Salem, NC (US)

(72) Inventors: Waldemar Debinski, Winston-Salem, NC (US); Hetal Pandya, Wintson-Salem, NC (US); Denise Mazess Herpai, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 12 days.

(21) Appl. No.: 15/045,557

(22) Filed: Feb. 17, 2016

(65) Prior Publication Data

US 2016/0175399 A1 Jun. 23, 2016

Related U.S. Application Data

(63) Continuation of application No. 13/264,473, filed as application No. PCT/US2010/031386 on Apr. 16, 2010, now Pat. No. 9,296,785.

(60) Provisional application No. 61/170,378, filed on Apr. 17, 2009.

(51) Int. Cl.

| | |
|---|---|
| ***A61K 38/20*** | (2006.01) |
| ***A61K 47/48*** | (2006.01) |
| ***C07K 7/06*** | (2006.01) |
| ***C07K 7/08*** | (2006.01) |
| ***A61K 38/08*** | (2006.01) |
| ***A61K 38/10*** | (2006.01) |
| ***C07K 14/54*** | (2006.01) |
| *A61K 38/00* | (2006.01) |

(52) U.S. Cl.

CPC .......... *A61K 38/2086* (2013.01); *A61K 38/08* (2013.01); *A61K 38/10* (2013.01); *A61K 47/48246* (2013.01); *A61K 47/48261* (2013.01); *C07K 7/06* (2013.01); *C07K 7/08* (2013.01); *C07K 14/5437* (2013.01); *A61K 38/00* (2013.01); *C07K 2319/01* (2013.01); *C07K 2319/55* (2013.01)

(58) Field of Classification Search

CPC .................................................. A61K 38/2086

See application file for complete search history.

(56) References Cited

U.S. PATENT DOCUMENTS

| | | | | |
|---|---|---|---|---|
| 5,208,020 | A | 5/1993 | Chari et al. | |
| 5,264,588 | A | 11/1993 | Nicolaou et al. | |
| 5,328,984 | A | 7/1994 | Pastan et al. | |
| 5,614,191 | A | 3/1997 | Puri et al. | |
| 5,677,178 | A | 10/1997 | McCormick | |
| 5,712,374 | A | 1/1998 | Kunstmann et al. | |
| 5,714,586 | A | 2/1998 | Kunstmann et al. | |
| 5,773,001 | A | 6/1998 | Hamann et al. | |
| 5,919,456 | A | 7/1999 | Puri et al. | |
| 6,214,559 | B1 | 4/2001 | Collins et al. | |
| 6,296,843 | B1 | 10/2001 | Debinski | |
| 6,428,788 | B1 | 8/2002 | Debinski et al. | |
| RE38,008 | E | 2/2003 | Abrams et al. | |
| 6,518,061 | B1 | 2/2003 | Puri et al. | |
| 6,528,487 | B1 * | 3/2003 | Heavner .......... | C07K 14/70564 514/19.1 |
| 6,576,232 | B1 | 6/2003 | Debinski et al. | |
| 6,630,576 | B2 | 10/2003 | Debinski | |
| 6,884,581 | B2 | 4/2005 | Debinski et al. | |
| 6,884,603 | B2 | 4/2005 | Debinski et al. | |
| 6,949,245 | B1 | 9/2005 | Sliwkowski | |
| 7,078,030 | B2 | 7/2006 | Johnson et al. | |
| 7,338,929 | B2 | 3/2008 | Debinski et al. | |
| 7,351,797 | B1 | 4/2008 | Hahn et al. | |
| 7,402,652 | B2 | 7/2008 | Miller | |
| 7,468,418 | B2 | 12/2008 | Iversen et al. | |
| 7,517,964 | B2 | 4/2009 | Govindan et al. | |
| 7,598,068 | B2 | 10/2009 | Debinski et al. | |
| 7,901,942 | B2 | 3/2011 | Kamilie et al. | |
| 7,960,361 | B2 | 6/2011 | Debinski et al. | |
| 8,343,461 | B2 | 1/2013 | Debinski et al. | |
| 8,362,207 | B2 | 1/2013 | Debinski et al. | |
| 8,435,534 | B2 | 5/2013 | Debinski et al. | |
| 9,005,600 | B2 | 4/2015 | Debinski et al. | |
| 2001/0046498 | A1 | 11/2001 | Ruoslahti et al. | |
| 2003/0129132 | A1 | 7/2003 | Puri et al. | |
| 2004/0023337 | A1 | 2/2004 | Heavner et al. | |
| 2004/0142372 | A1 | 7/2004 | McCall et al. | |
| 2006/0099652 | A1 | 5/2006 | Gately et al. | |
| 2006/0177902 | A1 | 8/2006 | Collins et al. | |

FOREIGN PATENT DOCUMENTS

| | | |
|---|---|---|
| WO | WO 93/21232 | 10/1993 |
| WO | WO 94/11026 | 5/1994 |

OTHER PUBLICATIONS

Zakharov, Stanislav D. (FEBS Letters 336(1), 95-99, 1993).*
Ranganathan (Tetrahedron Letters 37(29), 5199-5202, 1996).*
Ostergaard (FEBS Letters 362(3), 306-308, 1995).*
Bernardi RJ et al. Immunonanoshells for targeted photothermal ablation in medulloblastoma and glioma: an in vitro evaluation using human cell lines. J Neurooncol. 2008; 86: 165-172.
International Search Report and Written Opinion, PCT/US2010/031386, dated Jul. 6, 2010.
Chart RVJ et al. Immunoconjugates containing novel maytansinoids: promising anticancer drugs. Cancer Research. 1992; 52: 127-131.
Pandya H et al. Molecular targeting of intracellular compartments specifically in cancer cells. Genes & Cancer. 2010; 1(5): 421-433.
Pandya H. Selection/construction and characterization of novel peptides and recombinant protein agents targeting interleukin 13 receptor alpha 2 in glioblastoma multiforme. Dissertation, Wake Forest University Graduate School of Arts and Sciences. Winston-Salem, North Carolina. May 2011. pp. i-xvi, 1-223.

(Continued)

*Primary Examiner* — Amber D Steele
(74) *Attorney, Agent, or Firm* — Myers Bigel, P.A.

(57) ABSTRACT

A targeting peptide that specifically binds to an IL13 receptor (e.g., wherein said targeting peptide is not an IL13 fragment) is described. The targeting peptide is optionally conjugated to at least one effector molecule. In some embodiments, the peptide specifically binds to the IL13Rα2 protein.

20 Claims, No Drawings

(56) References Cited

OTHER PUBLICATIONS

Landen CN et al. Therapeutic EphA2 gene targeting in vivo using neutral liposomal small interfering RNA delivery. Cancer Research. 2005; 65: 6910-6918.

Rege A et al. Amphipathic peptide-based fusion peptides and immunoconjugates for the targeted ablation of prostate cancer cells. Cancer Research. 2007; 67: 6368-6375.

Pandya H et al. An interleukin 13 receptor (alpha) 2-specific peptide homes to human glioblastoma multiforme xenografts. Neuro-Oncology. 2012; 14(1): 6-18.

Wang B et al. Nanoparticles functionalized with Pep-1 as potential glioma targeting delivery system via Interleukin 13 receptor (alpha)2-mediated endocytosis. Biomaterials. 2014; 35: 5897-5907.

* cited by examiner

IL-13 RECEPTOR BINDING PEPTIDES

GOVERNMENT FUNDING

This invention was made with United States government support under grant number RO1 CA 741451 from the National Institutes of Health. The United States government has certain rights to this invention.

RELATED APPLICATIONS

This application claims the benefit of U.S. patent application Ser. No. 13/264,473, filed Apr. 10, 2013, now allowed, which is a 35 U.S.C. § 371 national phase entry of PCT Application PCT/US2010/031386, filed Apr. 16, 2010, and published in English on Oct. 21, 2010, as International Publication No. WO 2010/121125, and which claims the benefit under 35 U.S.C. § 119(e) of U.S. Provisional Patent Application Ser. No. 61/170,378, filed Apr. 17, 2009, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. §1.821, entitled 9151-123TSCT_ST25.txt, 30,114 bytes in size, generated on Mar. 7, 2016, and filed via EFS-Web, is provided in lieu of a paper copy. This Sequence Listing is hereby incorporated by reference into the specification for its disclosures.

FIELD OF THE INVENTION

The present invention concerns IL-13 receptor binding proteins, compositions containing the same, and methods of use thereof.

BACKGROUND OF THE INVENTION

Cancer is now the number one cause of death in North America. Malignant tumors of the central nervous system (CNS) are the third leading cause of cancer-related deaths in adolescents and adults between the ages of 15 and 34, and in children, brain tumors are the leading cause of cancer death. Furthermore, the two-year survival rate for patients with glioblastoma multiforme (GBM), a high-grade glioma (HGG), grade IV, is less than 20% (Davis et al. (1998) J. Neurosurg. 88:1-10), and there has been a steady increase in the incidence of brain cancers during the last 20 years ("Reports from the front" (1995) Science 267:1414). Almost any cancer can metastasize to the CNS (Olson et al. (1974) Arch. Neurol. 30:122-136).

A common approach to the treatment of malignant gliomas involves surgery (Berger (1994) Sem. Oncol. 21:172-185), radiation therapy (Gunderson & Tepper, Eds. (2000) Clinical Radiation Oncology (Churchill-Livingstone, Pa.), pp 314-35), and various chemotherapeutic regimens (Lesser & Grossman (1994) Sem. Oncol. 21:220-235), but neither single nor multimodal treatments are curative. At present, treatment is implemented to improve or sustain neurological function of the patient, to diminish the size of the tumor growing intracranially, and to lengthen intervals between treatments. Thus, new and molecular-specific methods of HGG treatment are urgently needed.

SUMMARY OF THE INVENTION

A first aspect of the present invention is a targeting peptide that specifically binds to an IL13 receptor (e.g., wherein said targeting peptide is not an IL13 fragment), the targeting peptide optionally conjugated to at least one effector molecule. In some embodiments, the peptide specifically binds to the IL13Rα2 protein. In some embodiments, the peptide does not specifically bind to the IL-13Rα1 protein. In some embodiments, the peptide does not bind to the binding site for IL-13 on the IL13Rα2 protein (or does not competitively inhibit IL-13 binding to the IL13Rα2 protein). In some embodiments, the peptide is from 6 or 7 to 10, 15 or 20 amino acids in length.

When the targeting peptide is conjugated to at least one effector molecule (e.g., one or two effector molecules), the peptide has (in some embodiments) the structure A-B-C, wherein: A is the targeting peptide; B is a first effector molecule; and C is a second effector molecule (and in some embodiments, different from the first effector molecule). In some embodiments, B is a toxin. In some embodiments, C is an amphipathic antimicrobial peptide. In some embodiments, A is a targeting peptide that binds to the IL-13 binding site, while in other embodiments A is a targeting peptide that does not bind to the IL-13 binding site.

A further aspect of the invention is a nucleic acid that encodes a peptide (including conjugates) as described herein. A further aspect of the invention is a host cell that contains such a nucleic acid and expresses the encoded peptide.

A further aspect of the invention is a method of treating cancer in a subject in need thereof, comprising administering said subject a peptide as described herein in a treatment effective amount. In some embodiments the method further comprises concurrently administering the subject a second targeting peptide that specifically binds to an IL13 receptor, wherein said second targeting peptide is IL-13 or an active fragment thereof, and wherein said second targeting peptide has at least one effector molecule conjugated thereto (typically, an effector molecule different from the effector molecule conjugated to the first targeting peptide).

A further aspect of the invention is the use of a peptide as described herein for the treatment of cancer or for the preparation of a medicament for treating cancer.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents cited herein are to be incorporated herein by reference in their entirety.

A. Definitions

"Label" or "detectable group" as used herein may be any suitable label or detectable group detectable by spectroscopic, photochemical, biochemical, immunochemical, electrical, optical or chemical means including but not limited to biotin, fluorophores, antigens, porphyrins, and radioactive isotopes. Labels useful in the present invention include biotin for staining with labeled avidin or streptavidin conjugate, magnetic beads (e.g., Dynabeads™), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^{3}H$, $^{35}S$, $^{14}C$, or $^{32}P$), enzymes (e.g., hydrolases, particularly phosphatases such as alkaline phosphatase, esterases and glycosidases, or oxidoreductases, particularly peroxidases such as horseradish peroxidase, and the like), substrates, cofactors, inhibitors, chemiluminescent groups, chromogenic agents, and calorimetric labels such as colloidal gold or colored glass or plastic (e.g., polystyrene, polypropylene, latex, etc.) beads.

"Capping group" as used herein includes, but is not limited to, acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenylphosphinyl. The capping groups may consist of such groups as $R^{10}CO—$, $R^{10}—O—CO—$, $R^{10}—PO—$, $R^{10}—SO_2—$ and arylalkyl-; where $R^{10}$ is selected from the group consisting of H, alkyl, alkenyl, alkynyl, aryl, and arylalkyl.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower-alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

The alkyl, alkenyl, and alkynyl groups of the invention can be substituted or unsubstituted and are either unless otherwise specified. When substituted the alkyl, alkenyl or alkynyl groups of the invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Arylalkyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like, which may be substituted or unsubstituted as noted above.

"IL13" or "IL-13" as used herein refers to interleukin-13, which is a pleiotropic cytokine. IL-13 has approximately 30% sequence identity with IL4 and exhibits IL4-like activities on monocytes/macrophages and human B cells (Minty et al. (1993) Nature 362:248; McKenzie et al. (1987) Proc. Natl. Acad. Sci. USA 90:3735). In particular, IL-13 appears to be a potent regulator of inflammatory and immune responses. IL-13 can up-regulate the monocyte/macrophage expression of CD23 and MHC class I and class II antigens, down-regulate the expression of Fc.gamma, and inhibit antibody-dependent cytotoxicity. IL-13 can also inhibit nitric oxide production as well as the expression of pro-inflammatory cytokines (e.g., IL-1, IL-6, IL-8, IL-10 and IL-12) and chemokines (MIP-1, MCP), but enhance the production of IL-1.

"Recombinant" nucleic acid as used herein refers to a nucleic acid produced by combining two or more nucleic acid sequences from different sources, e.g., by use of molecular biology techniques, to form a new nucleic acid, e.g., a "heterologous" nucleic acid. The recombinant nucleic acid may be provided in the form of a "vector" or "delivery vector" in order to transform or transfect cells to contain the new nucleic acid. As used herein, a "vector" or "delivery vector" can be a viral or non-viral vector that is used to deliver a nucleic acid to a cell, tissue or subject.

A "recombinant" protein is a protein produced by a recombinant nucleic acid. The nucleic acid may or may not be inserted into the genome of a host cell. The nucleic acid may exist, e.g., in plasmid form in a host cell. Alternatively, the recombinant protein may be produced by in vitro translation of the recombinant nucleic acid.

An "isolated" protein or polypeptide means a protein or polypeptide that is separated or substantially free from at least some of the other components of the naturally occurring organism or virus, for example, the cell or viral structural components or other proteins or nucleic acids commonly found associated with the protein. As used herein, the "isolated" protein or polypeptide is at least about 25%, 30%, 40%, 50%, 60%, 70%, 75%, 80%, 85%, 90%, 95%, 97%, 98%, 99% or more pure (w/w).

"Subjects" as used herein are generally human subjects and includes, but is not limited to, cancer patients. The subjects may be male or female and may be of any race or ethnicity, including, but not limited to, Caucasian, African- American, African, Asian, Hispanic, Indian, etc. The subjects may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., screened for veterinary medicine or pharmaceutical drug development purposes.

"Cancer" or "cancers" that can be detected and/or treated by the compounds, compositions and methods described herein include, but are not limited to, breast cancer, bladder cancer, pancreatic cancer, colorectal cancer, head and neck cancer, thyroid cancer, prostate cancer, and brain cancer such as gliomas (e.g., GBM), etc.

"Effector molecule" as used herein includes therapeutic agents, detectable groups, targeting ligands, and delivery vehicles (e.g., antibodies, lipids, liposomes). See, e.g., U.S. Pat. No. 6,630,576.

"Therapeutic agent" as used herein may be any therapeutic agent including, but not limited to, genetic materials or agents, radionuclides, chemotherapeutic agents, and cytotoxic agents (See, e.g., U.S. Pat. No. 6,949,245 to Sliwkowski), and amphipathic antimicrobial peptides.

"Radionuclide" as described herein includes, but is not limited to, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$L, $^{125}$L, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117}$mSn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Chemotherapeutic agent" as used herein includes, but is not limited to, methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine. Other examples are found in U.S. Patent Application Publication 2006/0121539 (Debinski et al.), which is incorporated by reference herein in its entirety.

"Cytotoxic agent" or "toxic agent" as used herein includes, but is not limited to, maytansinoids and maytansinoid analogs, taxoids, CC-1065 and CC-1065 analogs, dolastatin and dolastatin analogs, ricin (or more particularly the ricin A chain), aclacinomycin, Diphtheria toxin, Monensin, Verrucarin A, Abrin, Tricothecenes, and *Pseudomonas* exotoxin A, taxol, cytochalasin B, gramicidin D, ethidium bromide, emetine, mitomycin, etoposide, tenoposide, antimitotic agents, such as the vinca alkaloids (e.g., vincristine and vinblastine), colchicin, anthracyclines, such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including, but not limited to, dactinomycin (formerly actinomycin), bleomycin, mithramycin, calicheamicin, and anthramycin (AMC)).

In some embodiments, cytotoxic agents include toxins such as *Pseudomonas* exotoxin, ricin, abrin, ribonuclease (RNase), DNase I, *Staphylococcal* enterotoxin-A, pokeweed antiviral protein, gelonin, diphtheria toxin, etc. See, e.g., U.S. Pat. No. 7,517,964. In some embodiments, *Pseudomonas* exotoxin or a Diphtheria toxin are preferred. See U.S. Pat. No. 5,328,984 to Pastan et al. and U.S. Pat. No. 6,296,843 to Debinski, which are each incorporated by reference herein in its entirety. *Pseudomonas* exotoxins can include, but are not limited to, *Pseudomonas* exotoxin A (PE). The *Pseudomonas* exotoxin can be modified such that it substantially lacks domain Ia, and in some embodiments *Pseudomonas* exotoxins include PE38QQR and PE4E. Diphtheria toxins can include DT390, a diphtheria toxin in which the native binding domain is eliminated. It will be appreciated that in various embodiments, the therapeutic agents can be attached to, e.g., the amino terminus or the carboxyl terminus.

"Amphipathic antimicrobial peptide" as used herein includes amphipathic peptides that induce apoptosis of cancer cells, presumably through their ability to depoarize mitochondrial membranes. K. Rege et al., *Cancer Res.* 67, 6368 (Jul. 1, 2007). Such peptides are, in general, from 10, 12 or 13 to 20, 30 or 40 amino acids in length, or more, and typically have an amphipathic alpha-helical structure. Examples include, but are not limited to, $(KLAKLAK)_2$, SEQ ID NO:1; $(KLAKKLA)_2$, SEQ ID NO:2; $(KAAKKAA)_2$, SEQ ID NO:3; and $(KLGKKLG)_2$, SEQ ID NO:4. See, e.g., Ruoslahti et al., U.S. Patent Application Publication No. 2001/0046498 (Nov. 29, 2001).

"Detectable group" as used herein includes, but is not limited to, radiolabels (e.g., 35S, $^{125}$I, $^{32}$P, $^{3}$H, $^{14}$C, $^{131}$I), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein, fluorescent proteins), a fluorescent protein including, but not limited to, a green fluorescent protein or one of its many modified forms, a nucleic acid segment in accordance with known techniques, and energy absorbing and energy emitting agents.

"Treat" "treating" or "treatment" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently administering" or "concurrently administer" as used herein means that the two or more compounds or compositions are administered closely enough in time to produce a combined effect (that is, concurrently may be simultaneously, or it may be two or more events occurring within a short time period before or after each other, e.g., sequentially). Simultaneous concurrent administration may be carried out by mixing the compounds prior to administration, or by administering the compounds at the same point in time but at different anatomic sites and/or by using different routes of administration.

The definitions and techniques described herein also apply to the IL-13 targeting peptides, toxin proteins, and other compounds and compositions mentioned hereinabove and hereinbelow.

B. Targeting Peptides that do not Bind to the IL-13 Binding Site

In some embodiments, the targeting peptides of the present invention are not IL-13 or IL-13 fragments, but instead are peptides that do not bind to the IL-13 binding site, but instead bind to a different binding site on the IL-13 receptor.

The single letter code for amino acids as used herein is: A (Ala), C (Cys), D (Asp), E (Glu), F (Phe), G (Gly), H (His), I (Ile), K (Lys), L (Leu), M (Met), N (Asn), P (Pro), Q (Gin), R (Arg), S (Ser), T (Thr), V (Val), W (Trp), and Y (Tyr)).

In some embodiments, targeting peptides of the present invention can have the general formula, from amino terminus to carboxy terminus, or alternatively from carboxy terminus to amino terminus, of FORMULA I (SEQ ID NO:5):

$$X—R^1—R^2—R^3—R^4—R^5—R^6R^7—Y \quad (I)$$

wherein:

$R^1$ is G or S;

$R^2$ is a negatively charged amino acid (for example E or D);

$R^3$ is a large hydrophobic amino acid (for example M, W, Y, or, I);

$R^4$ is a small amino acid (for example G, S or A);

$R^5$ is a large or aromatic amino acid (for example W, F, H or Y);

$R^6$ is a preferably hydrophobic or neutral amino acid (for example V, P, T or N);

$R^7$ is a positively charged amino acid (for example R, K or H); and

X and Y are as given below.

In other embodiments, targeting peptides of the present invention can have the general formula, from amino terminus to carboxy terminus, or alternatively from carboxy terminus to amino terminus, of FORMULA II (SEQ ID NO:6):

$$X—R^1—R^2—R^3—R^4—R^5—R^6—R^7—Y \quad (II)$$

wherein:

$R^1$ is a hydrophobic amino acid (for example L, A, I, V, or M);

$R^2$ is a preferably hydrophobic or neutral amino acid (for example P, V, T or N);

$R^3$ is a charged or uncharged polar amino acid (for example Q, N, D, E or H)

$R^4$ is a hydrophobic amino acid (for example L, A, I, V, or M);

$R^5$ is large or aromatic amino acid (for example W, F, H or Y);

$R^6$ is a hydrophobic amino acid (for example L, A, I, V, or M);

$R^7$ is large or aromatic amino acid (for example F, W, H or Y); and

X and Y are as described below.

In still other embodiments, targeting peptides of the present invention can have the general formula, from amino terminus to carboxy terminus, or alternatively from carboxy terminus to amino terminus, of FORMULA III (SEQ ID NO:7):

$$X—R^1—R^2—R^3—R^4—R^5—R^6—R^7—Y \quad (III)$$

wherein:

$R^1$ is S or G;

$R^2$ is a preferably hydrophobic or neutral amino acid (for example, P, V, T or N);

$R^3$ is large or aromatic amino acid (for example F, W, H or Y);

$R^4$ is a hydrophobic amino acid (for example, L, A, I, V, or M);

$R^5$ is large or aromatic amino acid (for example H, W, F, or Y);

$R^6$ is a hydrophobic amino acid (for example L, A, I, V, or M);

$R^7$ is a hydrophobic amino acid (for example L, A, I, V, or M); and

X and Y are as described below.

In Formulas I-III X and Y can each independently be present or absent and when present can each independently be a capping group, a linking group (or "linker", including non-amino acid linking groups, see, e.g., U.S. Pat. Nos. 7,468,418; 7,402,652; and 7,351,797), an amino acid (e.g. C, S or G) optionally terminated by a capping group or linking group, or a peptide consisting of from 2 to 6 or 10 additional amino acids optionally terminated by a capping group or linking group.

The amino acids of peptides of the invention may be in D form, L form, or a combination thereof.

Specific examples of targeting peptides of FORMULAS I-III include, but are not limited to those set forth in Tables 1-3 and Tables 4-6 below. These peptides may or may not have linking groups bonded to the carboxy terminus Linking groups as used herein are described in more detail below.

Active compounds of the present invention can be produced by any suitable means, including by synthetic organic chemical techniques or by recombinant techniques in which a nucleic acid that encodes the active compound is produced and introduced into a host cell (typically in the form of an expression vector) so that the encoded active compound (peptide, fusion peptide, etc.) is expressed therein. Expression vectors can be designed for expression of proteins or polypeptides in prokaryotic or eukaryotic cells. For example, polypeptides can be expressed in bacterial cells such as *E. coli*, insect cells (e.g., in the baculovirus expression system), yeast cells or mammalian cells. Suitable host cells are discussed further in Goeddel, Gene Expression Technology: Methods in Enzymology 185, Academic Press, San Diego, Calif. (1990). Examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al. (1983) Mol. Cell. Biol. 3:2156-2165) and the pVL series (Lucklow & Summers (1989) Virology 170:31-39).

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

C. Targeting Peptides that Bind to the IL-13 Binding Site

In some embodiments of the invention, the targeting peptide or agent is IL-13 or a fragment thereof that specifically binds the IL-13 receptor. Recombinant IL-13 is commercially available from a number of sources (e.g., R&D Systems, Minneapolis, Minn., and Sanofi Bio-Industries, Inc., Tervose, Pa.). Alternatively, a gene or cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al. (1993) supra and McKenzie (1987) supra). In addition, the expression of IL-13 as a component of a chimeric molecule is detailed below. Also contemplated is the use of specific IL-13 mutants as described in U.S. Pat. No. 6,884,603 (Debinski et al.).

One of skill in the art will appreciate that analogues or fragments of IL-13 will also specifically bind to the IL-13 receptor. For example, conservative substitutions of residues (e.g., a serine for an alanine or an aspartic acid for a glutamic acid) comprising native IL-13 will provide IL-13 analogues that also specifically bind to the IL-13 receptor. Thus, the term "IL-13," when used in reference to a targeting molecule, also includes fragments, analogues or peptide mimetics of IL-13 that also specifically bind to the IL-13 receptor. Further discussion of IL-13 as contemplated by the present invention can be found in U.S. Pat. No. 5,328,984 (Pastan et al.), U.S. Pat. No. 5,614,191 (Puri et al.), U.S. Pat. No. 5,919,456 (Puri et al.), U.S. Pat. No. 6,296,843 (Debinski), U.S. Pat. No. 6,428,788 (Debinski et al.), 6,518,061 (Puri et al.), 6,576,232 (Debinski et al.), U.S. Pat. No. 6,630,576 (Debinski), and U.S. Pat. No. 6,884,603 (Debinski et al.).

These targeting peptides can be coupled to or conjugated to effector molecules by any suitable technique, including those described further in "Conjugates" below.

D. Conjugates

Targeting peptides as described herein may be coupled to or conjugated to an effector molecule such as a diagnostic and/or therapeutic agent in accordance with any of a variety of techniques, such as those employed in the production of immunoconjugates. See, e.g., U.S. Pat. No. 6,949,245 to Sliwkowski.

In some embodiments, recombinant fusion chimera protein anti-cancer cytotoxins are composed of a carrier/ligand and an effector (catalyst). Carrier/ligands can be proteinaceous compounds, such as growth factors, cytokines, and monoclonal antibodies. Among effectors, bacterial toxins, such as *Pseudomonas* exotoxin A and Diphtheria toxin, or plant toxins, such as ricin may be utilized in some embodiments. The fusion protein is targeted only to cells expressing a target receptor/adaptor for a carrier/ligand. These targets internalize in response to carrier/ligand binding. Targets include, but are not limited to, protein receptors, antigens of various nature, adhesion molecules, gangliosides, etc. For example, EphA2 is over-expressed in a majority of patients with GBM and its ligand induces a receptor-mediated internalization once it binds the receptor (Walker-Daniels et al. (2002) Mol. Cancer Res. 1:79-87). The latter may be used for, e.g., recombinant bacterial toxin-containing cytotoxins to exert anti-tumor action (Debinski (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809; Debinski (2002) Cancer Invest. 20:801-809).

Chemotherapeutic agents useful in the generation of such active compounds include those described above. Conjugates of targeting peptide and one or more small molecule toxins, such as a calicheamicin, a maytansine (See U.S. Pat. No. 5,208,020), a trichothene, and CC 1065 are also contemplated herein. In some embodiments, conjugates of targeting peptide to *Pseudomonas* exotoxins are used (U.S. Pat. No. 5,328,984 to Pastan et al.).

In some embodiments of the invention, the targeting peptide conjugated to one or more maytansine molecules (e.g., about 1 to about 10 maytansine molecules per targeting peptide molecule). Maytansine may, for example, be converted to May-SS-Me which may be reduced to May-SH3 and reacted with modified targeting peptide (Chari et al. (1992) Cancer Res. 52: 127-131) to generate an active compound.

Another conjugate of interest includes a targeting peptide conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^1$, $\alpha_2^1$, $\alpha_3^1$, N-acetyl-$\gamma_1^1$, PSAG and $\theta_1^1$, (Hinman et al. (1993) Cancer Res. 53:3336-3342; Lode et al. (1998) Cancer Res. 58:2925-2928). See also U.S. Pat. Nos. 5,714,586, 5,712,374, 5,264,586, and 5,773,001.

Enzymatically active toxins and fragments thereof which can be used are described above and include *diphtheria* A chain, nonbinding active fragments of *diphtheria* toxin, exotoxin A chain (from *Pseudomonas aeruginosa*), ricin A chain, abrin A chain (from *Corrybacterium typhimuriae*), modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates a conjugate formed between active compounds and an antibody or a compound with nucleolytic activity (e.g., a ribonuclease or a DNA endonuclease such as a deoxyribonuclease; DNase).

A variety of radioactive isotopes or radionuclides are available for the production of radioconjugated compounds as described above.

In some embodiments, conjugates of a targeting agent and therapeutic agents or detectable groups may be made using a variety of bi-functional protein coupling agents such as N-succinimidyl-3-(2-pyridyldithiol)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin conjugate can be prepared as described in Vitetta et al. (1987) Science 238:1098. Carbon-14-labeled 1-isothiocyanatobenzyl-3-methyldiethylene triaminepentaacetic acid (MX-DTPA) is an exemplary chelating agent for conjugation of radionucleotide to the targeting peptide. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. (1992) Cancer Res. 52:127-131) may be used.

Alternatively, a fusion protein including the targeting agent and therapeutic agent or detectable group may be made, e.g. by recombinant techniques or peptide synthesis.

In yet another embodiment, the targeting agent may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the targeting peptide is fused to a *Pseudomonas exotoxin* or *Diptheria* toxin. (U.S. Pat. No. 5,328,984 to Pastan et al. and U.S. Pat. No. 6,296,843 to Debinski). *Pseudomonas* exotoxins include, but are not limited to, *Pseudomonas* exotoxin A (PE). The *Pseudomonas* exotoxin can be modified such that it substantially lacks domain Ia, and *Pseudomonas* exotoxins may further include PE38QQR and PE4E. *Diphtheria* toxins include DT390, a *diphtheria* toxin in which the native binding domain is eliminated. It will be appreciated that the toxin can be connected to either of the amino terminus, or the carboxyl terminus.

E. Pharmaceutical Formulations and Methods

The active compounds, conjugates, and/or compositions thereof described herein may be formulated for administration in a pharmaceutical carrier in accordance with known techniques. See, e.g., Remington, *The Science and Practice of Pharmacy* ($9^{th}$ Ed. 1995). In the manufacture of a pharmaceutical formulation according to the invention, the active compound(s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound(s) as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Particular routes of parenteral administration include intrathecal injection, including directly into the tumor or a tumor resection cavity, and intraventricular injection into a ventricle of the brain.

Active compounds and compositions may be administered by intratumor injection (including tumors in any region such as tumors of the brain), or in the case of brain tumors injection into a ventricle of the brain.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or composition. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

Further, the present invention provides liposomal formulations of the compounds disclosed herein and compositions thereof. The technology for forming liposomal suspensions is well known in the art. When the compound or composition thereof is an aqueous-soluble composition, using conventional liposome technology, the same may be incorporated into lipid vesicles. In such an instance, due to the water solubility of the compound or composition, the compound or composition will be substantially entrained within the hydrophilic center or core of the liposomes. The lipid layer employed may be of any conventional composition and may either contain cholesterol or may be cholesterol-free. When the compound or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

Liposomal formulations containing the compounds disclosed herein or compositions thereof (e.g., ephrinA1 in monomeric form, or a conjugate thereof; IL-13 conjugates, and Fra-1 conjugates), may be lyophilized to produce a lyophilizate, which may be reconstituted with a pharmaceutically acceptable carrier, such as water, to regenerate a liposomal suspension. Examples of liposomal formulations that can be used include the neutral lipid 1,2-dioleoyl-sn-glycero-3-phosphatidylcholine (DPOC) (See, e.g., Landen Jr. et al. (2005) Cancer Res. 65:6910-6918).

Other pharmaceutical compositions may be prepared from the water-insoluble compounds disclosed herein, or compositions thereof, such as aqueous base emulsions. In such an instance, the composition will contain a sufficient amount of pharmaceutically acceptable emulsifying agent to emulsify the desired amount of the compound or composition thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

As a general proposition, the initial pharmaceutically effective amount of the active compound or composition administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of active compound, depending on the pattern of pharmacokinetic decay that the practitioner wishes to achieve.

The active compound(s) is suitably administered to the patient at one time or over a series of treatments. Depending on the type and severity of the disease, about 1 μg/kg to 15 mg/kg (e.g. 0.1-20 mg/kg) of active compound(s) is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The preferred dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 4 mg/kg, followed by a weekly maintenance dose of about 2 mg/kg of the active compound. However, other dosage regimens may be useful. The progress of this therapy is easily monitored by conventional techniques and assays.

Subjects treated by the methods of the present invention can also be administered one or more additional therapeutic agents. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

Subjects may also be treated by radiation therapy, including, but not limited to, external beam radiotherapy, which may be at any suitable dose (e.g., 20 to 70 Gy or more per tumor, typically delivered over a fractionated schedule).

Pharmaceutical compositions containing targeting agent in unlabeled form may be administered to subjects as blocking reagents, in like manner as described in Abrams et al., U.S. Pat. No. RE38,008, in conjunction with the administration of targeting agent coupled to a therapeutic group.

Targeting peptide coupled to a diagnostic group may also be used in vitro as histological reagents on tissue samples, where binding of the IL-13 receptor is indicative of cancer tissue in the tissue sample.

F. Double-Targeting Methods

Because targeting peptides of the invention do not bind to the IL-13 receptor at the same site as IL-13, these peptides provide a way to double-target the IL-13 receptor, and cells carrying the same, with two different effector molecules (e.g., a detectable group and a therapeutic group, a first therapeutic group and a second, different, therapeutic group, etc.) Such targeting peptides, including recombinant IL-13 and including peptides having various effector molecules bound thereto, are known and described in (for example) U.S. Pat. No. 6,630,765 to Debinski (the disclosure of which is incorporated by reference herein in its entirety. Such targeting peptides may be administered concurrently with targeting peptides that do not bind to the IL-13 receptor as at the same site as IL-13, and may be administered in accordance with known techniques or variations thereof that will be apparent to those skilled in the art based on the present disclosure.

EXAMPLE 1

Isolation and Characterization of IL-13Rα2-Specific Heptapeptides

We have been conducting a search for small peptides that would bind specifically to IL-13Rα2. To isolate the peptides binding to IL-13Rα2, we used the peptide phage-display library. Phage-display is a technology wherein peptide libraries are presented on the surface of filamentous M13 phages. We screened a heptapeptide phage display library, Ph.D-C7C (New England Biolabs) with a diversity of $1.2\times10^9$ different peptides, for peptides specifically binding to the IL-13Rα2 receptor. In our strategy, the phage library was repetitively panned using GBM cell lines which over-express the IL-13Rα2 receptor (G26-H2 and SnB19pCDNA) and corresponding cell lines, which do not express the IL-13Rα2 receptor (G26-V2 and SnB19asIL-13Rα2). Phages were eluted from IL-13Rα2 positive cells and subjected to additional binding/amplification cycles to enrich for IL-13Rα2 binding peptides (see Tables 1-2 below). After 4 rounds of panning, we identified 3 different peptide phage clones (see Table 3 below). ELISA experiments further confirmed that these 3 peptide phage clones bound to the IL-13Rα2/Fc receptor chimera protein and not to the control IgG-Fc and BSA proteins. Moreover, ELISA experiments including another IL-13 receptor proteins, IL-13Rα1, demonstrated that one of the peptides is truly specific for the IL-13Rα2 protein. Moreover, a 400× excess of the IL-13 ligand did not block the peptide's binding to the IL-13Rα2. This result suggests that the peptide is binding to the IL-13Rα2 receptor at the site other than its ligand binding site. Thus, we were able to identify specific hepta-peptides that bind to IL-13Rα2 and which can potentially be further developed for diagnostic, imaging and therapeutic interventions for GBM.

TABLE 1

Phage DNA sequences- Method 1- Sequenced 8 phages from each.

| | | | |
|---|---|---|---|
| G26 cell line- Phages | | | |
| G26-1 | Cys-Ser-Thr-Ser-Asn-Val-Leu-Val-Cys | C-S-T-S-N-V-L-V-C | (SEQ ID NO: 8) |
| G26-2 | Cys-Thr-Gln-Gly-Ser-Gly-lys-Ala-Cys | C-T-Q-G-S-G-K-A-C | (SEQ ID NO: 9) |
| G26-3 | Cys-Thr-Asn-Thr-Thr-Val-Pro-Phe-Cys | C-T-N-T-T-V-P-F-C | (SEQ ID NO: 10) |
| G26-4 | Cys-Ser-Gly-Pro-Tyr-Lys-His-Leu-Cys | C-S-G-P-Y-K-H-L-C | (SEQ ID NO: 11) |
| G26-5 | Cys-Thr-Thr-Thr-His-Thr-Pro-Thr-Cys | C-T-T-T-H-T-P-T-C | (SEQ ID NO: 12) |
| G26-6 | Cys-Pro-Thr-Asn-Thr-Gly-Gln-Ser-Cys | C-P-T-N-T-G-Q-S-C | (SEQ ID NO: 13) |
| G26-7 | Cys-Ser-Ser-Asn-Tyr-Trp-His-Gln-Cys | C-S-S-N-Y-W-H-Q-C | (SEQ ID NO: 14) |
| G26-8 | Cys-Asn-Thr-Pro-Met-Ser-Arg-Thr-Cys | C-N-T-P-M-S-R-T-C | (SEQ ID NO: 15) |
| Snb19 cell line- Phages | | | |
| SnB19-1 | No sequence | | |
| SnB19-2 | Cys-Thr-Gly-His-Thr-Leu-Asn-His-Cys | C-T-G-H-T-L-N-H-C | (SEQ ID NO: 16) |
| SnB19-3 | Cys-Leu-Thr-Pro-Leu-Pro-Arg-Pro-Cys | C-L-T-P-L-P-R-P-C | (SEQ ID NO: 17) |
| SnB19-4 | Cys-Ser-Pro-Glu-His-Leu-Gln-Gln-Cys | C-S-P-E-H-L-Q-Q-C | (SEQ ID NO: 18) |
| SnB19-5 | Cys-Lys-Gln-Pro-Thr-Pro- * -Ala-Cys | C-K-Q-P-T-P-*-A-C | (SEQ ID NO: 19) |
| SnB19-6 | Cys-Pro-Asp-His-Pro-Met-Tyr-Ala-Cys | C-P-D-H-P-M-Y-A-C | (SEQ ID NO: 20) |
| SnB19-7 | Cys-His-Ser-Ala-Ser-Ser-Pro-Val-Cys | C-H-S-A-S-S-P-V-C | (SEQ ID NO: 21) |
| SnB19-8 | Cys-Ala-Leu-Asp-Trp-Ile-Gly-Thr-Cys | C-A-L-D-W-I-G-T-C | (SEQ ID NO: 22) |

TABLE 2

Phage DNA sequences- Method 2- Sequenced phages from each cell line

| | | SEQ ID NO | | SEQ ID NO |
|---|---|---|---|---|
| Snb19 cell line- Phages | | | | |
| SnB19-1 | TGTCTGCCTCAGCTTTGGCTGTTTTGC | 23 | ***CLPQLWLFC*** | 24 |
| SnB19-2 | TGTAGTCCGTTTCTGCATCTGCTTTGC | 25 | ***CSPFLHLLC*** | 26 |

TABLE 2-continued

Phage DNA sequences- Method 2- Sequenced phages from each cell line

| | | SEQ ID NO | | SEQ ID NO |
|---|---|---|---|---|
| SnB19-3 | TGTCTTCCGTTTGTGCATTGGTTGTGC | 27 | CLPFVHWLC | 28 |
| SnB19-4 | No sequence | | | |
| SnB19-5 | TGTCGGCCTATTTCGCCGAATATGTGC | 29 | CRPISPNMC | 30 |
| SnB19-6 | TGTCTGCCTCAGCTTTGGCTGTTTTGC | 23 | ***CLPQLWLFC*** | 24 |
| SnB19-7 | TGTCTGCCTCAGCTTTGGCTGTTTTGC | 23 | ***CLPQLWLFC*** | 24 |
| SnB19-8 | TGTGGGTTGCCGGGGCAGATGCGTTGC | 31 | CGLPGQMRC | 32 |
| SnB19-9 | TGTCATAGTAATACGCCTGCTTTTTGC | 33 | CHSNTPAFC | 34 |
| SnB19-10 | TGTCATCCTCTTAATCAGATGCGGTGC | 35 | CHPLNQMRC | 36 |
| SnB19-11 | TGTATTCCGTTTGTGCATTGGTTGTGC | 37 | CIPFVHWLC | 38 |
| SnB19-12 | TGTCCGGATACGAAGCCTACTTGGTGC | 39 | CPDTKPTWC | 40 |
| SnB19-13 | TGTCTGCCTCAGCTTTGGCTGTTTTGC | 23 | ***CLPQLWLFC*** | 24 |
| SnB19-14 | TGTGTGGTGAATAAGCATGGGGCTTGC | 41 | CVVNKHGAC | 42 |
| SnB19-15 | No sequence | | | |
| SnB19-16 | TGTCATCCTATGCTGCCTTCGCAGTGC | 43 | CHPMLPSQC | 44 |
| SnB19-17 | No sequence | | | |
| SnB19-18 | TGTACTGCGTCGAAGAATCTTTTGTGC | 45 | CTASKNLLC | 46 |
| SnB19-19 | TGTAGTCCGTTTCTGCATCTGCTTTGC | 25 | ***CLPQLWLFC*** | 24 |
| SnB19-20 | TGTAATGGGATTTCTAATAATCTGTGC | 47 | CNGISNNLC | 48 |
| SnB19-21 | To be resequenced | | | |
| SnB19-22 | To be resequenced | | | |
| SnB19-23 | TGTACGTCGTTTCATGCGCCTGATTGC | 49 | CTSFHAPDC | 50 |
| SnB19-24 | TGTACGCCTCTTCATTCTCCGCATTGC | 51 | CTPLHSPHC | 53 |
| SnB19-25 | TGTAGTCCGTTTCTGCATCTGCTTTGC | 25 | ***CSPFLHLLC*** | 26 |
| SnB19-26 | TGTTCTTTTATTACGCCGGGGCGTTGC | 53 | CSPITPGRC | 54 |
| SnB19-27 | TGTACGACGGATGCGCATTCTCAGTGC | 55 | CTTDAHSQC | 56 |
| SnB19-28 | No sequence | | | |
| SnB19-29 | To be resequenced | | | |

TABLE 2-continued

Phage DNA sequences- Method 2- Sequenced phages from each cell line

| | | SEQ ID NO | | SEQ ID NO |
|---|---|---|---|---|
| SnB19-30 | TGTCTGTCTGAGAC GCATTCGCAGTGC | 57 | CLSETHSQC | 58 |
| **G26 cell line Phages** | | | | |
| G26 1 | TGTGGTGAGATGGG GTGGGTTCGTTGC | 59 | *CGEMGWVRC* | 60 |
| G26 2 | TGTGGTGAGATGGG GTGGGTTCGTTGC | 59 | *CGEMGWVRC* | 60 |
| G26 3 | TGTGGTGAGATGGG GTGGGTTCGTTGC | 59 | *CGEMGWVRC* | 60 |
| G26 4 | TGTGGTGAGATGGG GTGGGTTCGTTGC | 59 | *CGEMGWVRC* | 60 |
| G26 5 | TGTGGTGAGATGGG GTGGGTTCGTTGC | 59 | *CGEMGWVRC* | 60 |
| G26 6 | TGTGGTGAGATGGG GTGGGTTCGTTGC | 59 | *CGEMGWVRC* | 60 |
| G26 7 | TGTGGTGAGATGGG GTGGGTTCGTTGC | 59 | *CGEMGWVRC* | 60 |
| G26 8 | TGTGGTGAGATGGG GTGGGTTCGTTGC | 59 | *CGEMGWVRC* | 60 |
| G26 9 | TGTGGTGAGATGGG GTGGGTTCGTTGC | 59 | *CGEMGWVRC* | 60 |
| G26 10 | TGTGGTGAGATGGG GTGGGTTCGTTGC | 59 | *CGEMGWVRC* | 60 |
| G26 11 | TGTGGTGAGATGGG GTGGGTTCGTTGC | 59 | *CGEMGWVRC* | 60 |
| G26 12 | TGTGGTGAGATGGG GTGGGTTCGTTGC | 59 | *CGEMGWVRC* | 60 |
| G26 13 | TGTGGTGAGATGGG GTGGGTTCGTTGC | 59 | *CGEMGWVRC* | 60 |
| G26 14 | TGTGGTGAGATGGG GTGGGTTCGTTGC | 59 | *CGEMGWVRC* | 60 |
| G26 15 | TGTGGTGAGATGGG GTGGGTTCGTTGC | 59 | *CGEMGWVRC* | 60 |
| G26 16 | TGTGGTGAGATGGG GTGGGTTCGTTGC | 59 | *CGEMGWVRC* | 60 |
| G26 17 | TGTGGTGAGATGGG GTGGGTTCGTTGC | 59 | *CGEMGWVRC* | 60 |
| G26 18 | TGTGGTGAGATGGG GTGGGTTCGTTGC | 59 | *CGEMGWVRC* | 60 |
| G26 19 | TGTGGTGAGATGGG GTGGGTTCGTTGC | 59 | *CGEMGWVRC* | 60 |
| G26 20 | TGTGGTGAGATGGG GTGGGTTCGTTGC | 59 | *CGEMGWVRC* | 60 |
| G26 21 | TGTGGTGAGATGGG GTGGGTTCGTTGC | 59 | *CGEMGWVRC* | 60 |
| G26 22 | TGTGGTGAGATGGG GTGGGTTCGTTGC | 59 | *CGEMGWVRC* | 60 |
| G26 23 | TGTGGTGAGATGGG GTGGGTTCGTTGC | 59 | *CGEMGWVRC* | 60 |
| G26 24 | TGTGGTGAGATGGG GTGGGTTCGTTGC | 59 | *CGEMGWVRC* | 60 |
| G26 25 | TGTGGTGAGATGGG GTGGGTTCGTTGC | 59 | *CGEMGWVRC* | 60 |
| G26 26 | TGTGGTGAGATGGG GTGGGTTCGTTGC | 59 | *CGEMGWVRC* | 60 |
| G26 27 | TGTGGTGAGATGGG GTGGGTTCGTTGC | 59 | *CGEMGWVRC* | 60 |
| G26 28 | TGTGGTGAGATGGG GTGGGTTCGTTGC | 59 | *CGEMGWVRC* | 60 |
| G26 29 | TGTTCTATGCAGGC TCTTCCGTTTTGC | 61 | CSMQALPFC | 62 |
| G26 30 | TGTCAGACGGAGGG TCCTAATAGGTGC | 63 | CQTEGPNRC | 64 |

TABLE 3

| Sequences of three peptides | |
|---|---|
| Peptide A | *CGEMGWVRC* (SEQ ID NO: 60)<br>N-ACGEMGWVRCGGGS-C (SEQ ID NO: 65) |
| Peptide B | ***CLPQLWLFC*** (SEQ ID NO: 24)<br>ACLPQLWLFCGGGS (SEQ ID NO: 66) |
| Peptide C | ***CSPFLHLLC*** (SEQ ID NO: 26)<br>ACSPFLHLLCGGGS (SEQ ID NO: 67) |

Notes

1. The peptide library -Ph.D-C7C has heptapeptides constrained by cysteines and also all the heptapeptides have some additional amino acids which are found in all the peptides. Hence for example in the peptide A, in addition to the unique 7 amino acids, we have 2 cysteines and 5 additional amino acids, i.e. alanine at the N terminal and GGGS (SEQ ID NO: 116) at the end making the total length of the peptide to be 14 amino acids
2. All the amino acids are from N terminal to C terminal in orientation, with the N terminal charged and the C terminal not-charged

EXAMPLE 2

Multi-Level Specific Targeting of Cancer Cells

We have designed double-specificity therapeutic delivery systems, which not only specifically recognize cancer cells, but also enable intracellular distribution of anti-cancer agents to their respective sites of action, like the cytosol, mitochondria and/or nucleus. Some cationic peptides lyse negatively charged mitochondrial membranes of a eukaryotic cell, leading to initiation of caspase-3 dependent cell death. We have chosen one such peptide, $(KLAKLAK)_2$ [SEQ ID NO:1, KK] to target the mitochondria of glioblastoma multiforme (GBM) brain tumor cells. To target GBM cells, we exploited interleukin 13 receptor alpha 2 (IL-13Rα2), an IL-13 plasma membrane receptor which is over-expressed in 75% of GBM patients. To enable intracytosolic delivery of the KK peptide mediated first by the IL-13Rα2, we use *Pseudomonas* exotoxin A (PE) domain II [D2] based delivery vector. D2 of PE is responsible for the processing and translocation of the internalized toxin and any other protein/agent fused to its C-terminal end from the endosome to the cytosol. Thus, we have generated single chain fusion proteins composed of IL-13, D2 and KK: IL-13.D2 and IL-13.D2.KK, respectively. These proteins were expressed in BL21 (λDE3) *E. coli* under the bacteriophage T7 promoter control and were further processed and purified by the FPLC system to >95% purity. Both proteins retained binding to the IL-13Rα2 and contained similar, marginal levels of endotoxins. Treatment of U-251 MG and U-87 MG GBM cells, over-expressors of IL-13Rα2, with 1 to 20 μM of IL-13.D2.KK severely altered morphology of GBM cells whereas equimolar concentrations of the IL-13.D2 and the KK peptide alone did not have any measurable effect on the cells. Furthermore, treatment of T98G GBM cells, which do not over-express the IL-13Rα2 with the IL-13.D2.KK showed much less pronounced morphological changes. Thus, IL-13.D2.KK specifically recognizes cells over-expressing IL-13Rα2 and delivers the apoptosis-inducing peptide to the mitochondria of GBM cells. This is the first example of GBM targeted, double-specificity, pro-apoptotic therapy that leads to cell death.

EXAMPLE 3

Additional examples of active compounds of the present invention include those set forth in Tables 4-6 below.

TABLE 4

| Additional Peptides of Formula I |
|---|
| SEMGWVRC (SEQ ID NO: 68) |
| GDMGWVR (SEQ ID NO: 69) |
| SDWGWVR (SEQ ID NO: 70) |
| GDYGWVR (SEQ ID NO: 71) |
| SEIGWVR (SEQ ID NO: 72) |
| GEISWVR (SEQ ID NO: 73) |
| GEMAWVR (SEQ ID NO: 74) |
| GEMGFVR (SEQ ID NO: 75) |
| GEMGHVR (SEQ ID NO: 76) |
| GEMSYVR (SEQ ID NO: 77) |
| GEMGWPR (SEQ ID NO: 78) |
| GEMGWTR (SEQ ID NO: 79) |
| GEMGWNK (SEQ ID NO: 80) |
| GEMGWNH (SEQ ID NO: 81) |

TABLE 5

| Additional Peptides of Formula II |
|---|
| APQLWLF (SEQ ID NO: 82) |
| IPQLWLF (SEQ ID NO: 83) |
| VPQLWLF (SEQ ID NO: 84) |
| MPQLWLF (SEQ ID NO: 85) |
| LVQLWLF (SEQ ID NO: 86) |
| LTQLWLF (SEQ ID NO: 87) |
| LNQLWLF (SEQ ID NO: 88) |
| LPNLWLF (SEQ ID NO: 89) |
| LPDLWLF (SEQ ID NO: 90) |
| LPELWLF (SEQ ID NO: 91) |
| LPHLWLF (SEQ ID NO: 92) |
| LPQAFAW (SEQ ID NO: 93) |
| LPQIFIH (SEQ ID NO: 94) |
| LPQVHVY (SEQ ID NO: 95) |
| LPQMYMY (SEQ ID NO: 96) |
| MNHMYMY (SEQ ID NO: 97) |
| VTEVHVH (SEQ ID NO: 98) |

TABLE 6

| Additional Peptides of Formula III |
|---|
| GPFLHLL (SEQ ID NO: 99) |
| SVFLHLL (SEQ ID NO: 100) |
| STFLHLL (SEQ ID NO: 101) |
| SNWLHLL (SEQ ID NO: 102) |
| SPHLHLL (SEQ ID NO: 103) |
| SPYLHLL (SEQ ID NO: 104) |
| SPFAHLL (SEQ ID NO: 105) |
| SPFIHLL (SEQ ID NO: 106) |
| SPFVHLL (SEQ ID NO: 107) |
| SPFMHLL (SEQ ID NO: 108) |
| SPFLWLL (SEQ ID NO: 109) |
| SPFLFAA (SEQ ID NO: 110) |
| SPFLFII (SEQ ID NO: 111) |
| SPFLHVV (SEQ ID NO: 112) |
| SPFLYMM (SEQ ID NO: 113) |
| GNYMYMM (SEQ ID NO: 114) |
| GTHVFVI (SEQ ID NO: 115) |

The foregoing is illustrative of the present invention, and is not to be construed as limiting thereof. The invention is defined by the following claims, with equivalents of the claims to be included therein.

That which is claimed is:

1. A targeting peptide that specifically binds to an IL13 receptor, wherein said targeting peptide is not an IL13 fragment, said peptide having a structure of FORMULA II (SEQ ID NO:6):

$$X—R^1—R^2—R^3—R^4—R^5—R^6—R^7—Y \quad (II)$$

wherein:

$R^1$ is L, A, I, or M;
$R^2$ is P, V, or T;
$R^3$ is Q, N, D, or E
$R^4$ is L, A, I, V, or M;
$R^5$ is W, F, or H;
$R^6$ is L, A, I, V, or M;
$R^7$ is F, W, H or Y; and
X and Y can each independently be present or absent and when present can each independently be a capping group, a linking group, an amino acid optionally terminated by a capping group or linking group, or a peptide consisting of from 2 to 10 additional amino acids optionally terminated by a capping group or linking group.

2. The peptide of claim 1, wherein said peptide is selected from the group consisting of:

CLPQLWLFC (SEQ ID NO:24); and
ACLPQLWLFCGGGS (SEQ ID NO:66).

3. The peptide claim 1, wherein said peptide is conjugated to at least one effector molecule.

4. The peptide of claim 3, wherein said at least one effector molecule consists of one effector molecule.

5. The peptide of claim 3, wherein said at least one effector molecule consists of two effector molecules.

6. The peptide of claim 5, wherein said peptide has the structure A-B-C, wherein:

A is said targeting peptide;
B is a first effector molecule; and
C is a second effector molecule.

7. The peptide of claim 6, wherein B is a toxin and C is an amphipathic antimicrobial peptide.

8. The peptide of claim 7, wherein said toxin is selected from the group consisting of diphtheria toxin and *Pseudomonas* exotoxin.

9. The peptide of claim 7, wherein said amphipathic antimicrobial peptide comprises a sequence selected from the group consisting of: $(KLAKLAK)_2$, SEQ ID NO:1; $(KLAKKLA)_2$, SEQ ID NO:2; $(KAAKKAA)_2$, SEQ ID NO:3; and $(KLGKKLG)_2$, SEQ ID NO:4.

10. The peptide of claim 7, wherein said at least one effector molecule comprises a therapeutic agent, a detectable group, a lipid, or a liposome.

11. A targeting peptide that specifically binds to an IL13 receptor, wherein said targeting peptide is not an IL13 fragment, said peptide having a structure of FORMULA III (SEQ ID NO:7):

$$X—R^1—R^2—R^3—R^4—R^5—R^6—R^7—Y \quad (III)$$

wherein:

$R^1$ is S or G;
$R^2$ is P, V, T or N;
$R^3$ is F, W, H or Y;
$R^4$ is L, A, I, V, or M;
$R^5$ is H, W, F, or Y;
$R^6$ is L, A, I, V, or M;
$R^7$ is L, A, I, V, or M; and
X and Y can each independently be present or absent and when present can each independently be a capping group, a linking group, an amino acid optionally terminated by a capping group or linking group, or a peptide consisting of from 2 to 10 additional amino acids optionally terminated by a capping group or linking group.

12. The peptide of claim 11, wherein said peptide is selected from the group consisting of:

CSPFLHLLC (SEQ ID NO:26); and
ACSPFLHLLCGGGS (SEQ ID NO:67).

13. An expression vector comprising a nucleic acid that encodes a targeting peptide that specifically binds to an IL13 receptor, wherein said targeting peptide is not an IL13 fragment, said peptide having a structure of FORMULA II (SEQ ID NO:6):

$$X—R^1—R^2—R^3—R^4—R^5—R^6—R^7—Y \quad (II)$$

wherein:

$R^1$ is L, A, I, or M;
$R^2$ is P, V, or T;
$R^3$ is Q, N, D, or E
$R^4$ is L, A, I, V, or M;
$R^5$ is W, F, or H;
$R^6$ is L, A, I, V, or M;
$R^7$ is F, W, H or Y; and
X and Y can each independently be present or absent and when present can each independently be a capping group, a linking group, an amino acid optionally terminated by a capping group or linking group, or a peptide consisting of from 2 to 10 additional amino acids optionally terminated by a capping group or linking group.

14. A host cell that contains a nucleic acid of claim 13 and expresses the encoded peptide.

15. A method of treating cancer in a subject in need thereof, comprising administering said subject a peptide of claim 1 in a treatment effective amount.

16. The method of claim 15, wherein said cancer is selected from the group consisting of breast cancer, bladder cancer, pancreatic cancer, colorectal cancer, head and neck cancer, thyroid cancer, prostate cancer, and gliomas.

17. The method of claim 15, wherein said cancer is glioblastoma multiforme.

18. The method of claim 15, further comprising concurrently administering said subject a second targeting peptide that specifically binds to an IL13 receptor, wherein said second targeting peptide is IL-13, a mutant of IL-13, or an IL-13 receptor binding fragment thereof.

19. A method of delivering at least one effector molecule to a cell of interest, comprising:

contacting a compound of claim 1 to a cell of interest (e.g., a eukaryotic cells) under conditions in which said compound is internalized therein.

20. The method of claim 19, wherein said effector molecule is a detectable group.

* * * * *

SEQUENCE LISTING

<160> NUMBER OF SEQ ID NOS: 116

<210> SEQ ID NO 1
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 1

Lys Leu Ala Lys Leu Ala Lys Lys Leu Ala Lys Leu Ala Lys
1               5                   10

<210> SEQ ID NO 2
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 2

Lys Leu Ala Lys Lys Leu Ala Lys Leu Ala Lys Lys Leu Ala
1               5                   10

<210> SEQ ID NO 3
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 3

Lys Ala Ala Lys Lys Ala Ala Lys Ala Ala Lys Lys Ala Ala
1               5                   10

<210> SEQ ID NO 4
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 4

Lys Leu Gly Lys Lys Leu Gly Lys Leu Gly Lys Lys Leu Gly
1               5                   10

<210> SEQ ID NO 5
<211> LENGTH: 7
<212> TYPE: PRT
<213> ORGANISM: Artificial
<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is G or S
<220> FEATURE:
<221> NAME/KEY: MISC_FEATURE
<222> LOCATION: (2)..(2)
<223> OTHER INFORMATION: Xaa is a negatively charged amino acid (e.g. Glu or Asp)
<220> FEATURE:
<221> NAME/KEY: MISC_FEATURE
<222> LOCATION: (3)..(3)
<223> OTHER INFORMATION: Xaa is a large hydrophobic amino acid (e.g. Met, Trp, Tyr or Ile)

<220> FEATURE:
<221> NAME/KEY: MISC_FEATURE
<222> LOCATION: (4)..(4)
<223> OTHER INFORMATION: Xaa is a small amino aicd (e.g. Gly, Ser or Ala)
<220> FEATURE:
<221> NAME/KEY: MISC_FEATURE
<222> LOCATION: (5)..(5)
<223> OTHER INFORMATION: Xaa is a large or aromatic amino acid (e.g. Trp, Phe, His or Tyr)
<220> FEATURE:
<221> NAME/KEY: MISC_FEATURE
<222> LOCATION: (6)..(6)
<223> OTHER INFORMATION: Xaa is preferably a hydrophobic or neutral amino acid (e.g. Val, Pro, Thr or Asn)
<220> FEATURE:
<221> NAME/KEY: MISC_FEATURE
<222> LOCATION: (7)..(7)
<223> OTHER INFORMATION: Xaa is a positiviely charged amino acid (e.g. Arg, Lys or His)

<400> SEQUENCE: 5

```
Xaa Xaa Xaa Xaa Xaa Xaa Xaa
1               5
```

<210> SEQ ID NO 6
<211> LENGTH: 7
<212> TYPE: PRT
<213> ORGANISM: Artificial
<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is a hydrophobic amino acid (e.g. Leu, Ala, Ile, Val or Met)
<220> FEATURE:
<221> NAME/KEY: MISC_FEATURE
<222> LOCATION: (2)..(2)
<223> OTHER INFORMATION: Xaa is a preferably hydrophobic or neutral amino acid (e.g. Pro, Val, Thr or Asn)
<220> FEATURE:
<221> NAME/KEY: MISC_FEATURE
<222> LOCATION: (3)..(3)
<223> OTHER INFORMATION: Xaa is a charged or uncharged polar amino acid (e.g. Gln, Asn, Asp, Glu or His)
<220> FEATURE:
<221> NAME/KEY: MISC_FEATURE
<222> LOCATION: (4)..(4)
<223> OTHER INFORMATION: Xaa is a hydrophobic amino acid (e.g. Leu, Ala, Ile, Val or Met)
<220> FEATURE:
<221> NAME/KEY: MISC_FEATURE
<222> LOCATION: (5)..(5)
<223> OTHER INFORMATION: Xaa is a large or aromatic amino acid (e.g. Trp, Phe, His or Tyr)
<220> FEATURE:
<221> NAME/KEY: MISC_FEATURE
<222> LOCATION: (6)..(6)
<223> OTHER INFORMATION: Xaa is a hydrophobic amino acid (e.g. Leu, Ala, Ile, Val or Met)
<220> FEATURE:
<221> NAME/KEY: MISC_FEATURE
<222> LOCATION: (7)..(7)
<223> OTHER INFORMATION: Xaa is a large or aromatic amino acid (e.g. Trp, Phe, His or Tyr)

<400> SEQUENCE: 6

```
Xaa Xaa Xaa Xaa Xaa Xaa Xaa
1               5
```

<210> SEQ ID NO 7
<211> LENGTH: 7
<212> TYPE: PRT
<213> ORGANISM: Artificial

-continued

<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is Ser or Gly
<220> FEATURE:
<221> NAME/KEY: MISC_FEATURE
<222> LOCATION: (2)..(2)
<223> OTHER INFORMATION: Xaa is a preferably hydrophobic or neutral amino aicd (e.g. Pro, Val, Thr or Asn)
<220> FEATURE:
<221> NAME/KEY: MISC_FEATURE
<222> LOCATION: (3)..(3)
<223> OTHER INFORMATION: Xaa is a large or aromatic amino aicd (e.g. Phe, Trp, His or Tyr)
<220> FEATURE:
<221> NAME/KEY: MISC_FEATURE
<222> LOCATION: (4)..(4)
<223> OTHER INFORMATION: Xaa is a hydrophobic amino aicd (e.g. Leu, Ala, Ile, Var or Met)
<220> FEATURE:
<221> NAME/KEY: MISC_FEATURE
<222> LOCATION: (5)..(5)
<223> OTHER INFORMATION: Xaa is a large or aromatic amino aicd (e.g. Phe, Trp, His or Tyr)
<220> FEATURE:
<221> NAME/KEY: MISC_FEATURE
<222> LOCATION: (6)..(6)
<223> OTHER INFORMATION: Xaa is a hydrophobic amino aicd (e.g. Leu, Ala, Ile, Var or Met)
<220> FEATURE:
<221> NAME/KEY: MISC_FEATURE
<222> LOCATION: (7)..(7)
<223> OTHER INFORMATION: Xaa is a hydrophobic amino aicd (e.g. Leu, Ala, Ile, Var or Met)

<400> SEQUENCE: 7

Xaa Xaa Xaa Xaa Xaa Xaa Xaa
1               5

<210> SEQ ID NO 8
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 8

Cys Ser Thr Ser Asn Val Leu Val Cys
1               5

<210> SEQ ID NO 9
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 9

Cys Thr Gln Gly Ser Gly Lys Ala Cys
1               5

<210> SEQ ID NO 10
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 10

Cys Thr Asn Thr Thr Val Pro Phe Cys
1               5

<210> SEQ ID NO 11
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 11

Cys Ser Gly Pro Tyr Lys His Leu Cys
1               5

<210> SEQ ID NO 12
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 12

Cys Thr Thr Thr His Thr Pro Thr Cys
1               5

<210> SEQ ID NO 13
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 13

Cys Pro Thr Asn Thr Gly Gln Ser Cys
1               5

<210> SEQ ID NO 14
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 14

Cys Ser Ser Asn Tyr Trp His Gln Cys
1               5

<210> SEQ ID NO 15
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 15

Cys Asn Thr Pro Met Ser Arg Thr Cys
1               5

<210> SEQ ID NO 16
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 16

Cys Thr Gly His Thr Leu Asn His Cys
1               5

<210> SEQ ID NO 17
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 17

Cys Leu Thr Pro Leu Pro Arg Pro Cys
1               5

<210> SEQ ID NO 18
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 18

Cys Ser Pro Glu His Leu Gln Gln Cys
1               5

<210> SEQ ID NO 19
<211> LENGTH: 9
<212> TYPE: PRT
<213> ORGANISM: Artificial
<220> FEATURE:
<223> OTHER INFORMATION: Isolated IL-13R(alpha)2 binding peptide
<220> FEATURE:
<221> NAME/KEY: MISC_FEATURE
<222> LOCATION: (7)..(7)
<223> OTHER INFORMATION: Xaa is unknown

<400> SEQUENCE: 19

Cys Lys Gln Pro Thr Pro Xaa Ala Cys
1               5

<210> SEQ ID NO 20
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 20

Cys Pro Asp His Pro Met Tyr Ala Cys
1               5

<210> SEQ ID NO 21
<211> LENGTH: 9
<212> TYPE: PRT
<213> ORGANISM: Artificial
<220> FEATURE:
<223> OTHER INFORMATION: Isolated IL-13R(alpha)2 binding peptide

<400> SEQUENCE: 21

Cys His Ser Ala Ser Ser Pro Val Cys
1               5

<210> SEQ ID NO 22
<211> LENGTH: 9
<212> TYPE: PRT
<213> ORGANISM: Artificial

-continued

```
<220> FEATURE:
<223> OTHER INFORMATION: Isolated IL-13R(alpha)2 binding peptide

<400> SEQUENCE: 22

Cys Ala Leu Asp Trp Ile Gly Thr Cys
1               5


<210> SEQ ID NO 23
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 23

tgt ctg cct cag ctt tgg ctg ttt tgc                                27
Cys Leu Pro Gln Leu Trp Leu Phe Cys
1               5


<210> SEQ ID NO 24
<211> LENGTH: 9
<212> TYPE: PRT
<213> ORGANISM: Artificial
<220> FEATURE:
<223> OTHER INFORMATION: Synthetic Construct

<400> SEQUENCE: 24

Cys Leu Pro Gln Leu Trp Leu Phe Cys
1               5


<210> SEQ ID NO 25
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 25

tgt agt ccg ttt ctg cat ctg ctt tgc                                27
Cys Ser Pro Phe Leu His Leu Leu Cys
1               5


<210> SEQ ID NO 26
<211> LENGTH: 9
<212> TYPE: PRT
<213> ORGANISM: Artificial
<220> FEATURE:
<223> OTHER INFORMATION: Synthetic Construct

<400> SEQUENCE: 26

Cys Ser Pro Phe Leu His Leu Leu Cys
1               5


<210> SEQ ID NO 27
<211> LENGTH: 27
<212> TYPE: DNA
<213> ORGANISM: Artificial
```

-continued

<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 27 tgt ctt ccg ttt gtg cat tgg ttg tgc 27
Cys Leu Pro Phe Val His Trp Leu Cys
1 5

<210> SEQ ID NO 28
<211> LENGTH: 9
<212> TYPE: PRT
<213> ORGANISM: Artificial
<220> FEATURE:
<223> OTHER INFORMATION: Synthetic Construct

<400> SEQUENCE: 28

Cys Leu Pro Phe Val His Trp Leu Cys
1 5

<210> SEQ ID NO 29
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 29 tgt cgg cct att tcg ccg aat atg tgc 27
Cys Arg Pro Ile Ser Pro Asn Met Cys
1 5

<210> SEQ ID NO 30
<211> LENGTH: 9
<212> TYPE: PRT
<213> ORGANISM: Artificial
<220> FEATURE:
<223> OTHER INFORMATION: Synthetic Construct

<400> SEQUENCE: 30

Cys Arg Pro Ile Ser Pro Asn Met Cys
1 5

<210> SEQ ID NO 31
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 31 tgt ggg ttg ccg ggg cag atg cgt tgc 27
Cys Gly Leu Pro Gly Gln Met Arg Cys
1 5

-continued

<210> SEQ ID NO 32
<211> LENGTH: 9
<212> TYPE: PRT
<213> ORGANISM: Artificial
<220> FEATURE:
<223> OTHER INFORMATION: Synthetic Construct

<400> SEQUENCE: 32

Cys Gly Leu Pro Gly Gln Met Arg Cys
1 5

<210> SEQ ID NO 33
<211> LENGTH: 27
<212> TYPE: DNA
<213> ORGANISM: Artificial
<220> FEATURE:
<223> OTHER INFORMATION: Phage DNA sequence coding for IL13R(alpha)2 binding peptide
<220> FEATURE:
<221> NAME/KEY: CDS
<222> LOCATION: (1)..(27)

<400> SEQUENCE: 33 tgt cat agt aat acg cct gct ttt tgc 27
Cys His Ser Asn Thr Pro Ala Phe Cys
1 5

<210> SEQ ID NO 34
<211> LENGTH: 9
<212> TYPE: PRT
<213> ORGANISM: Artificial
<220> FEATURE:
<223> OTHER INFORMATION: Synthetic Construct

<400> SEQUENCE: 34

Cys His Ser Asn Thr Pro Ala Phe Cys
1 5

<210> SEQ ID NO 35
<211> LENGTH: 27
<212> TYPE: DNA
<213> ORGANISM: Artificial
<220> FEATURE:
<223> OTHER INFORMATION: Phage DNA sequence coding for IL13R(alpha)2 binding peptide
<220> FEATURE:
<221> NAME/KEY: CDS
<222> LOCATION: (1)..(27)

<400> SEQUENCE: 35 tgt cat cct ctt aat cag atg cgg tgc 27
Cys His Pro Leu Asn Gln Met Arg Cys
1 5

<210> SEQ ID NO 36
<211> LENGTH: 9
<212> TYPE: PRT
<213> ORGANISM: Artificial
<220> FEATURE:
<223> OTHER INFORMATION: Synthetic Construct

<400> SEQUENCE: 36

Cys His Pro Leu Asn Gln Met Arg Cys
1 5

<210> SEQ ID NO 37
<211> LENGTH: 27
<212> TYPE: DNA
<213> ORGANISM: Artificial

-continued

<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 37 tgt att ccg ttt gtg cat tgg ttg tgc 27
Cys Ile Pro Phe Val His Trp Leu Cys
1 5

<210> SEQ ID NO 38
<211> LENGTH: 9
<212> TYPE: PRT
<213> ORGANISM: Artificial
<220> FEATURE:
<223> OTHER INFORMATION: Synthetic Construct

<400> SEQUENCE: 38

Cys Ile Pro Phe Val His Trp Leu Cys
1 5

<210> SEQ ID NO 39
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 39 tgt ccg gat acg aag cct act tgg tgc 27
Cys Pro Asp Thr Lys Pro Thr Trp Cys
1 5

<210> SEQ ID NO 40
<211> LENGTH: 9
<212> TYPE: PRT
<213> ORGANISM: Artificial
<220> FEATURE:
<223> OTHER INFORMATION: Synthetic Construct

<400> SEQUENCE: 40

Cys Pro Asp Thr Lys Pro Thr Trp Cys
1 5

<210> SEQ ID NO 41
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 41 tgt gtg gtg aat aag cat ggg gct tgc 27
Cys Val Val Asn Lys His Gly Ala Cys
1 5

```
<210> SEQ ID NO 42
<211> LENGTH: 9
<212> TYPE: PRT
<213> ORGANISM: Artificial
<220> FEATURE:
<223> OTHER INFORMATION: Synthetic Construct

<400> SEQUENCE: 42

Cys Val Val Asn Lys His Gly Ala Cys
1               5


<210> SEQ ID NO 43
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 43

tgt cat cct atg ctg cct tcg cag tgc                                  27
Cys His Pro Met Leu Pro Ser Gln Cys
1               5


<210> SEQ ID NO 44
<211> LENGTH: 9
<212> TYPE: PRT
<213> ORGANISM: Artificial
<220> FEATURE:
<223> OTHER INFORMATION: Synthetic Construct

<400> SEQUENCE: 44

Cys His Pro Met Leu Pro Ser Gln Cys
1               5


<210> SEQ ID NO 45
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 45

tgt act gcg tcg aag aat ctt ttg tgc                                  27
Cys Thr Ala Ser Lys Asn Leu Leu Cys
1               5


<210> SEQ ID NO 46
<211> LENGTH: 9
<212> TYPE: PRT
<213> ORGANISM: Artificial
<220> FEATURE:
<223> OTHER INFORMATION: Synthetic Construct

<400> SEQUENCE: 46

Cys Thr Ala Ser Lys Asn Leu Leu Cys
1               5


<210> SEQ ID NO 47
<211> LENGTH: 27
<212> TYPE: DNA
<213> ORGANISM: Artificial
```

-continued

```
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 47

tgt aat ggg att tct aat aat ctg tgc                                  27
Cys Asn Gly Ile Ser Asn Asn Leu Cys
1               5


<210> SEQ ID NO 48
<211> LENGTH: 9
<212> TYPE: PRT
<213> ORGANISM: Artificial
<220> FEATURE:
<223> OTHER INFORMATION: Synthetic Construct

<400> SEQUENCE: 48

Cys Asn Gly Ile Ser Asn Asn Leu Cys
1               5


<210> SEQ ID NO 49
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 49

tgt acg tcg ttt cat gcg cct gat tgc                                  27
Cys Thr Ser Phe His Ala Pro Asp Cys
1               5


<210> SEQ ID NO 50
<211> LENGTH: 9
<212> TYPE: PRT
<213> ORGANISM: Artificial
<220> FEATURE:
<223> OTHER INFORMATION: Synthetic Construct

<400> SEQUENCE: 50

Cys Thr Ser Phe His Ala Pro Asp Cys
1               5


<210> SEQ ID NO 51
<211> LENGTH: 27
<212> TYPE: DNA
<213> ORGANISM: Artificial
<220> FEATURE:
<223> OTHER INFORMATION: Phage DNA sequence coding for IL13R(alpha)2
      binding peptide
<220> FEATURE:
<221> NAME/KEY: CDS
<222> LOCATION: (1)..(27)

<400> SEQUENCE: 51

tgt acg cct ctt cat tct ccg cat tgc                                  27
Cys Thr Pro Leu His Ser Pro His Cys
1               5
```

<210> SEQ ID NO 52
<211> LENGTH: 9
<212> TYPE: PRT
<213> ORGANISM: Artificial
<220> FEATURE:
<223> OTHER INFORMATION: Synthetic Construct

<400> SEQUENCE: 52

Cys Thr Pro Leu His Ser Pro His Cys
1 5

<210> SEQ ID NO 53
<211> LENGTH: 27
<212> TYPE: DNA
<213> ORGANISM: Artificial
<220> FEATURE:
<223> OTHER INFORMATION: Phage DNA sequence coding for IL13R(alpha)2 binding peptide
<220> FEATURE:
<221> NAME/KEY: CDS
<222> LOCATION: (1)..(27)

<400> SEQUENCE: 53 tgt tct ttt att acg ccg ggg cgt tgc 27
Cys Ser Phe Ile Thr Pro Gly Arg Cys
1 5

<210> SEQ ID NO 54
<211> LENGTH: 9
<212> TYPE: PRT
<213> ORGANISM: Artificial
<220> FEATURE:
<223> OTHER INFORMATION: Synthetic Construct

<400> SEQUENCE: 54

Cys Ser Phe Ile Thr Pro Gly Arg Cys
1 5

<210> SEQ ID NO 55
<211> LENGTH: 27
<212> TYPE: DNA
<213> ORGANISM: Artificial
<220> FEATURE:
<223> OTHER INFORMATION: Phage DNA sequence coding for IL13R(alpha)2 binding peptide
<220> FEATURE:
<221> NAME/KEY: CDS
<222> LOCATION: (1)..(27)

<400> SEQUENCE: 55 tgt acg acg gat gcg cat tct cag tgc 27
Cys Thr Thr Asp Ala His Ser Gln Cys
1 5

<210> SEQ ID NO 56
<211> LENGTH: 9
<212> TYPE: PRT
<213> ORGANISM: Artificial
<220> FEATURE:
<223> OTHER INFORMATION: Synthetic Construct

<400> SEQUENCE: 56

Cys Thr Thr Asp Ala His Ser Gln Cys
1 5

<210> SEQ ID NO 57
<211> LENGTH: 27
<212> TYPE: DNA
<213> ORGANISM: Artificial

<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 57 tgt ctg tct gag acg cat tcg cag tgc 27
Cys Leu Ser Glu Thr His Ser Gln Cys
1 5

<210> SEQ ID NO 58
<211> LENGTH: 9
<212> TYPE: PRT
<213> ORGANISM: Artificial
<220> FEATURE:
<223> OTHER INFORMATION: Synthetic Construct

<400> SEQUENCE: 58

Cys Leu Ser Glu Thr His Ser Gln Cys
1 5

<210> SEQ ID NO 59
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 59 tgt ggt gag atg ggg tgg gtt cgt tgc 27
Cys Gly Glu Met Gly Trp Val Arg Cys
1 5

<210> SEQ ID NO 60
<211> LENGTH: 9
<212> TYPE: PRT
<213> ORGANISM: Artificial
<220> FEATURE:
<223> OTHER INFORMATION: Synthetic Construct

<400> SEQUENCE: 60

Cys Gly Glu Met Gly Trp Val Arg Cys
1 5

<210> SEQ ID NO 61
<211> LENGTH: 27
<212> TYPE: DNA
<213> ORGANISM: Artificial
<220> FEATURE:
<223> OTHER INFORMATION: Phage DNA sequence coding for IL13R(alpha)2
binding peptide
<220> FEATURE:
<221> NAME/KEY: CDS
<222> LOCATION: (1)..(27)

<400> SEQUENCE: 61 tgt tct atg cag gct ctt ccg ttt tgc 27
Cys Ser Met Gln Ala Leu Pro Phe Cys
1 5

<210> SEQ ID NO 62
<211> LENGTH: 9
<212> TYPE: PRT
<213> ORGANISM: Artificial
<220> FEATURE:
<223> OTHER INFORMATION: Synthetic Construct

<400> SEQUENCE: 62

Cys Ser Met Gln Ala Leu Pro Phe Cys
1 5

<210> SEQ ID NO 63
<211> LENGTH: 27
<212> TYPE: DNA
<213> ORGANISM: Artificial
<220> FEATURE:
<223> OTHER INFORMATION: Phage DNA sequence coding for IL13R(alpha)2 binding peptide
<220> FEATURE:
<221> NAME/KEY: CDS
<222> LOCATION: (1)..(27)

<400> SEQUENCE: 63 tgt cag acg gag ggt cct aat agg tgc 27
Cys Gln Thr Glu Gly Pro Asn Arg Cys
1 5

<210> SEQ ID NO 64
<211> LENGTH: 9
<212> TYPE: PRT
<213> ORGANISM: Artificial
<220> FEATURE:
<223> OTHER INFORMATION: Synthetic Construct

<400> SEQUENCE: 64

Cys Gln Thr Glu Gly Pro Asn Arg Cys
1 5

<210> SEQ ID NO 65
<211> LENGTH: 14
<212> TYPE: PRT
<213> ORGANISM: Artificial
<220> FEATURE:
<223> OTHER INFORMATION: IL-13R(alpha)2 binding peptide sequence

<400> SEQUENCE: 65

Ala Cys Gly Glu Met Gly Trp Val Arg Cys Gly Gly Gly Ser
1 5 10

<210> SEQ ID NO 66
<211> LENGTH: 14
<212> TYPE: PRT
<213> ORGANISM: Artificial
<220> FEATURE:
<223> OTHER INFORMATION: IL-13R(alpha)2 binding peptide sequence

<400> SEQUENCE: 66

Ala Cys Leu Pro Gln Leu Trp Leu Phe Cys Gly Gly Gly Ser
1 5 10

<210> SEQ ID NO 67
<211> LENGTH: 14
<212> TYPE: PRT
<213> ORGANISM: Artificial
<220> FEATURE:
<223> OTHER INFORMATION: IL-13R(alpha)2 binding peptide sequence

<400> SEQUENCE: 67

Ala Cys Ser Pro Phe Leu His Leu Leu Cys Gly Gly Gly Ser
1 5 10

<210> SEQ ID NO 68
<211> LENGTH: 8
<212> TYPE: PRT
<213> ORGANISM: Artificial
<220> FEATURE:
<223> OTHER INFORMATION: IL-13R(alpha)2 binding peptide sequence

<400> SEQUENCE: 68

Ser Glu Met Gly Trp Val Arg Cys
1 5

<210> SEQ ID NO 69
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 69

Gly Asp Met Gly Trp Val Arg
1 5

<210> SEQ ID NO 70
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 70

Ser Asp Trp Gly Trp Val Arg
1 5

<210> SEQ ID NO 71
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 71

Gly Asp Tyr Gly Trp Val Arg
1 5

<210> SEQ ID NO 72
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 72

Ser Glu Ile Gly Trp Val Arg
1 5

<210> SEQ ID NO 73
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 73

Gly Glu Ile Ser Trp Val Arg
1               5

<210> SEQ ID NO 74
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 74

Gly Glu Met Ala Trp Val Arg
1               5

<210> SEQ ID NO 75
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 75

Gly Glu Met Gly Phe Val Arg
1               5

<210> SEQ ID NO 76
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 76

Gly Glu Met Gly His Val Arg
1               5

<210> SEQ ID NO 77
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 77

Gly Glu Met Ser Tyr Val Arg
1               5

<210> SEQ ID NO 78
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 78

Gly Glu Met Gly Trp Pro Arg
1               5

<210> SEQ ID NO 79
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 79

Gly Glu Met Gly Trp Thr Arg
1 5

<210> SEQ ID NO 80
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 80

Gly Glu Met Gly Trp Thr Arg
1 5

<210> SEQ ID NO 81
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 81

Gly Glu Met Gly Trp Asn His
1 5

<210> SEQ ID NO 82
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 82

Ala Pro Gln Leu Trp Leu Phe
1 5

<210> SEQ ID NO 83
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 83

Ile Pro Gln Leu Trp Leu Phe
1 5

<210> SEQ ID NO 84
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 84

Val Pro Gln Leu Trp Leu Phe
1 5

<210> SEQ ID NO 85
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 85

Met Pro Gln Leu Trp Leu Phe
1 5

<210> SEQ ID NO 86
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 86

Leu Val Gln Leu Trp Leu Phe
1 5

<210> SEQ ID NO 87
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 87

Leu Thr Gln Leu Trp Leu Phe
1 5

<210> SEQ ID NO 88
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 88

Leu Asn Gln Leu Trp Leu Phe
1 5

<210> SEQ ID NO 89
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 89

Leu Pro Asn Leu Trp Leu Phe
1 5

<210> SEQ ID NO 90
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 90

Leu Pro Asp Leu Trp Leu Phe
1 5

<210> SEQ ID NO 91
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 91

Leu Pro Glu Leu Trp Leu Phe
1               5

<210> SEQ ID NO 92
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 92

Leu Pro His Leu Trp Leu Phe
1               5

<210> SEQ ID NO 93
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 93

Leu Pro Gln Ala Phe Ala Trp
1               5

<210> SEQ ID NO 94
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 94

Leu Pro Gln Ile Phe Ile His
1               5

<210> SEQ ID NO 95
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 95

Leu Pro Gln Val His Val Tyr
1               5

<210> SEQ ID NO 96
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 96

Leu Pro Gln Met Tyr Met Tyr
1               5

<210> SEQ ID NO 97
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 97

Met Asn His Met Tyr Met Tyr
1 5

<210> SEQ ID NO 98
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 98

Val Thr Glu Val His Val His
1 5

<210> SEQ ID NO 99
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 99

Gly Pro Phe Leu His Leu Leu
1 5

<210> SEQ ID NO 100
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 100

Ser Val Phe Leu His Leu Leu
1 5

<210> SEQ ID NO 101
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 101

Ser Thr Phe Leu His Leu Leu
1 5

<210> SEQ ID NO 102
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 102

Ser Asn Trp Leu His Leu Leu
1 5

<210> SEQ ID NO 103
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 103

Ser Pro His Leu His Leu Leu
1 5

<210> SEQ ID NO 104
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 104

Ser Pro Tyr Leu His Leu Leu
1 5

<210> SEQ ID NO 105
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 105

Ser Pro Phe Ala His Leu Leu
1 5

<210> SEQ ID NO 106
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 106

Ser Pro Phe Ile His Leu Leu
1 5

<210> SEQ ID NO 107
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 107

Ser Pro Phe Val His Leu Leu
1 5

<210> SEQ ID NO 108
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 108

Ser Pro Phe Met His Leu Leu
1 5

<210> SEQ ID NO 109
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 109

Ser Pro Phe Leu Trp Leu Leu
1 5

<210> SEQ ID NO 110
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 110

Ser Pro Phe Leu Phe Ala Ala
1 5

<210> SEQ ID NO 111
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 111

Ser Pro Phe Leu Phe Ile Ile
1 5

<210> SEQ ID NO 112
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 112

Ser Pro Phe Leu His Val Val
1 5

<210> SEQ ID NO 113
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 113

Ser Pro Phe Leu Tyr Met Met
1 5

<210> SEQ ID NO 114
<211> LENGTH: 7
<212> TYPE: PRT
<213> ORGANISM: Artificial
<220> FEATURE:
<223> OTHER INFORMATION: IL-13R(alpha)2 binding peptide sequence

<400> SEQUENCE: 114

Gly Asn Tyr Met Tyr Met Met
1 5

<210> SEQ ID NO 115
<211> LENGTH: 7
<212> TYPE: PRT
<213> ORGANISM: Artificial
<220> FEATURE:
<223> OTHER INFORMATION: IL-13R(alpha)2 binding peptide sequence -continued

```
<400> SEQUENCE: 115

Gly Thr His Val Phe Val Ile
1               5


<210> SEQ ID NO 116
<211> LENGTH: 4
<212> TYPE: PRT
<213> ORGANISM: Artificial
<220> FEATURE:
<223> OTHER INFORMATION: N-terminal IL-13R(alpha)2 binding peptide
      extension sequence

<400> SEQUENCE: 116

Gly Gly Gly Ser
1
```